United States Patent [19]

Duron et al.

[11] 4,236,892
[45] Dec. 2, 1980

[54] SEPARATION AND QUANTITATION OF COPROPORPHYRINS AND UROPORPHYRINS

[75] Inventors: Olga Duron, El Monte, Calif.; Richard J. Griffin, deceased, late of Lakewood, Colo.; by United Bank of Denver, N. A., personal representative, Denver, Colo.

[73] Assignee: Whale Scientific, Inc., Commerce City, Colo.

[21] Appl. No.: 965,429

[22] Filed: Dec. 1, 1978

[51] Int. Cl.³ ............... G01N 31/06; G01N 31/08; G01N 33/72; G01N 21/64
[52] U.S. Cl. .................................................. 23/230 B
[58] Field of Search ................................... 23/230 B

[56] References Cited
PUBLICATIONS

M. I. Walters, Am. Clin. Lab. Sci., 4(1), 29–35, (1974). Chemical Abstracts, 83:4091s (1975).

"Ion Exchangers in Org. and Biochem.", C. Calmon et al., eds., 335–337, Interscience, New York, 1957.
R. L. Searcy, "Diagnostic Biochemistry", 421–422, McGraw-Hill, New York, 1969.

*Primary Examiner*—Sidney Marantz
*Attorney, Agent, or Firm*—John E. Reilly

[57] ABSTRACT

Urinary porphyrin levels are assayed as a diagnosis technique for many disorders and abnormalities. Selective separation and quantitation of coproporphyrins (COPRO) and uroporphyrins (URO) are accomplished by adsorbing urine on an anionic exchange resin and selectively eluting the COPRO then the URO from the resin, followed by the determination of the amount of COPRO or URO in the respective eluates. In preferred methods the COPRO eluate is a diluted HCl and the eluate for URO is a more concentrated HCl; and the amount of COPRO or URO is determined quantitatively by fluorometric comparison with known concentrations of COPRO.

11 Claims, No Drawings

SEPARATION AND QUANTITATION OF COPROPORPHYRINS AND UROPORPHYRINS

BACKGROUND OF THE INVENTION

The present invention relates to methods for separating and quantifying urinary porphyrins, and more particularly relates to biological testing methods for separating and then determining the amount of coproporphyrin and uroporphyrin in human urine utilizing chemical analytical techniques involving anionic ion exchange.

Porphyrins are a group of organic pigments normally found as free compounds in minute quantities in the body. Porphyrins have been found to be of major importance to human metabolism. Porphyrins are not normally excreted in any significant amounts in the urine, and those disorders which lead to excretion of porphyrins are referred to as "porphyrinuria." Disorders of porphyrin metabolism are termed "porphyria".

Porphyrins detectable in urine have been divided into two primary fractions denoted as "coproporhyrins" and "uroporphyrins". Those porphyrins designated as "coproporphyrins" are extracted from urine treated with sodium carbonate and aqueous acetic acid and then extracted with ethyl acetate as taught by Schwartz et al "An improved method for the determination of urinary coprophyrin and evaluation of the factors influencing the analysis" J. LAB. CLIN. MED. 37, 843–859 (1951). The remaining porphyrins have been designated as "uroporphyrins" and are extracted from the aqueous phase by adsorption on aluminum oxide followed by dilution with 1.5 N HCl. Uroporphyrins are those porphyrins which are soluble in water but insoluble in ethyl acetate at a pH level of about 4 to 6.

The body contains large amounts of porphyrins as metal complexes which are associated with proteins e.g. hemoglobin, myoglobin, catalase, and cytochromes. Normally, only minimum amounts of free porphyrins are present in the body. However, the amounts of porphyrins found in the urine increase as a result of various malfunctions or problems such as vitamin deficiency, liver damage, (jaundice, infectious hepatitis, cirrosis), lead poisoning, and certain drugs (arsenic, carbon tetrachloride, benzine, and sulfomamides), or as problems in porphyrin metabolism such as congenital erythropoietic porphyria.

While in high concentrations the porphyrins are red to pink, they rarely appear in high enough concentrations in urine so that their color can be noticed. However, minute quantities fluoresce under ultraviolet light and are thus detectable.

Increased COPRO levels in urine are indicative of congenital erythropoietic porphyria and hepatic porphyria, associated with heavy metal poisoning, infectious hepatitis, cirrhosis, and various forms of anemia. Increased URO levels in urine are indicative of congenital erythropoietic porphyria, acute intermittent porphyria, and porphyria cutanea tarda.

Certain techniques and methodologies have been developed for qualitative detection of excreted porphyrins (porphyrinuria). For instance, ion exchange techniques have been utilized which typically require adsorption of a urine sample on an anionic ion exchange resin, elution of substantially all porphyrins with hydrochloric acid, and the determination of the presence or absence of free porphyrins by examining the eluate under long wavelength ultraviolet light whereby the presence of porphyrins is signaled by a pink fluorescence. However, this procedure indicates the presence of either or both COPRO and URO and does not provide for quantitative measurement of all the porphyrins or for the isolation and quantitation of either or both COPRO and URO.

Other quantitative methods of determination of COPRO and URO have been utilized. Perhaps the most widely used is that of Talman et al, "Porphyrins in Urine" Stand. Methods Clin. Chem. 2; 137 (1958). However, this method has not been widely adopted in clinical laboratories because it is multi-step, includes complex procedures, such as solvent extractions, and requires an extensive amount of time to complete each porphyrin determination. More recently Martinez et al "Spectrofluorometric Determination of Porphyrins in Urine" Clin. Chem. 17; 199 (1971) reported fluorometric methods of porphyrin analysis using ion exchange resins. However, these techniques do not include the separation of and selective quantitation of COPRO and URO. Sobel et al, "Separation and Quantitation of Copro Porphyrin and Uro Porphyrin in Urine" Clin. Chem. 20; 1397 (1974) discloses the separation and measurement of COPRO and URO in a system requiring concommitant ion exchange resins and solvent extractions. This latter technique has been questioned in terms of whether the eluates produce background fluoresence interference. Subsequently, Lavallee et al, "Compensation by Zinc Chelation for Fluorescent Background in Determining Copro Porphyrin and Uro Porphyrin in Urine" Clin. Chem. 23; 282 (1977) suggested the elimination of interference in the Sobel et al technique by adding zinc, in the form of $ZnCl_2$, to urine samples.

SUMMARY OF THE INVENTION

It has now been discovered that excretion, and specifically urine, can be simply and easily treated in such a manner as to provide both separation of COPRO and URO and quantitation of the amounts of COPRO and URO using ion exchange techniques. Briefly, the method consists of the steps of passing a urine sample through an anionic ion exchange resin column which adsorbs substantially all of the COPRO and URO, selectively eluting the COPRO and then the URO from the column using a first eluate which is specific to COPRO and a second eluate which removes URO and then measuring the concentrations of COPRO and URO in their respective eluates against a known standard. One suitable ion exchange column employs an ion exchange resin sold under the AMBERLITE IRA-400 name, manufactured and sold by Rohn & Haas of Philadelphia, Pa. It is commercially available from Whale Scientific, Inc., of Aurora, Colorado and is of the type described in U.S. Pat. No. 3,360,683. Where such commercially available columns are used they are provided in sealed and capped form, are filled with a packaging liquid, then are made operative by removal of the cap, inserting a funnel into the top of the column, cutting the bottom of the column, and draining the packaging liquid completely to waste. Other ion exchange columns can be utilized in the practice of the present invention, such as, for example, commercially available ion exchange columns with an aluminum oxide resin manufactured and sold by Bio-Rad Laboratories of Richmond, Calif. However, as will be explained in more detail hereinafter, modification of the columns will normally result in modification of the character of the eluate utilized in the practice of the present invention. In preferred embodiments, the eluate for COPRO is diluted HCl and the eluate for URO is a more concentrated HCl. The concentration of the HCl utilized to separate the COPRO or URO from the resin column is to some extent dependent upon the specific nature of the ion exchange resin utilized. In preferred embodiments, the measurement of the COPRO and URO concentrations is obtained utilizing a fluorometer and comparing their fluoresence against a known standard, as set forth in greater detail hereinafter.

The present invention requires either multiple steps, time consuming procedure, nor solvent extraction. It utilizes no organic solvents, and as such avoids the hazards and expense of organic solvents. Furthermore, the present invention requires no elaborate reagent preparation, no evaporation of eluates, and is simple and fast, with the entire procedure requiring only about 15–20 minutes. Furthermore, the methods of the present invention have been found to be reproducible and accurate. For purposes of comparing the prior art qualitative analysis technique with the present separation and quantitation technique, the two methods are set forth side by side below:

| Qualitative Method (Prior Art) | Quantitative Method |
|---|---|
| 24 hour urine sample | 24 hour urine sample |
| Aliquot (5 ml) passed through ion exchange resin columns (Adsorption of COPRO and URO) | Aliquot (5 ml) passed through ion exchange resin columns (Adsorption of COPRO and URO) |
| Wash with distilled water | Wash with distilled water |
| Elute COPRO and URO with 0.75 or 0.3 N HCl | Selectively elute COPRO with N 0.75 or 0.3 HCl |
| | Selectively elute URO with N 3.0 or 6.0 HCl |
| Examine eluate for porphyrin with long wavelength ultra-violet lamp. | Selectively measure the concentration of the COPRO and URO eluates against a known standard with a fluorometer. |

It is thus seen that by the expedient of utilizing relatively dilute hydrochloric acid as a first eluate, followed by the use of a more concentrated hydrochloric acid as a second eluate that COPRO and URO can be substantially completely separated from one another in the same urine sample followed by quantitative testing to determine both their concentrations.

The foregoing and other objects, features and advantages of the invention will be apparent from the following more particular description of the preferred embodiments of the invention.

DETAILED DESCRIPTION OF THE PREFERRED EMBODIMENT

As previously noted, the separation and quantitation methods of the present invention differ in the materials and methodology employed when compared with the prior qualitative process. However, utilizing substantially the same steps and many of the same components, the present invention provides selective separation of COPRO and URO and independent quantitative measurement of the separated COPRO and URO preferably by fluorometric analysis. Each of the preferred separations and quantitations referred to herein utilize the components referred to above. One procedure and order of utilizing the components is as follows:

EXAMPLE I

A 24 hour urine sample preserved in 5 gm. sodium carbonate is prepared for porphyrin determination. Adjust pH to 5.2±0.1. In most instances, about 5 gm of sodium carbonate is sufficient preservative. A 24 hour urine sample is most representative of the subject system, since due to functions of time, ambulation, nutrition, ultra-violet radiation, and other factors, including certain circadian rhythms, the biochemical system, including the urine, fluctuates throughout the day. As the porphyrin concentration may vary in each sample of urine over a 24 hour period, a 24 hour collection of urine offers the most consistent indication of porphyrin in the urine on a reproducible basis for each subject.

1. Label sufficient numbers of 50 ml beakers for patients and controls.
2. Add 5 ml of the urine sample to appropriate beaker.
3. Add 1 ml of 1 M Tris buffer pH 6.0 and adjust pH to 5.2±0.1 with 10% HCl.
4. Snip tip, and remove cap of as many resin columns as needed. Place in special rack and let drain. Label columns.
5. Insert funnel and add 3.0 ml of water to each column. Allow to drain.
6. Pour each buffered urine specimen and control (from steps 2 and 3) into its respective numbered column. (Set aside one column for the standard). Save one of the unknown urine samples that have passed through the column to dilute the coproporphyrin standard.
7. Add 5 ml of distilled water to each column. Let drain completely.
8. Place column in a corresponding numbered 25 ml graduated cylinder.
9. Elute each column with four 5 ml portions of 0.75 N HCl. Take the eluate to 25 ml volume with 0.75 HCl. Mix thoroughly using parafilm paper. This portion of the eluate contains the COPRO. Set aside and proceed to the following step.
10. Transfer the columns to a new set of graduated 25 ml cylinders. Label accordingly. To each column add 3.1 ml of 6.0 N HCl. Continue to elute each column with 10 ml distilled water. Take each eluate to 25 ml volume with distilled water; mix thoroughly with parafilm paper. This portion of the eluate contains the uroporphyrins. Set aside.
11. Prepare the coproporphyrin internal standard as follows:
    a. Dissolve the content of one Sigma vial which contains 5 micrograms (mcg) of coproporhyrin in exactly 10 ml of 1.5 N HCl. This is the stock standard solution. (0.5 mcg per 1 ml.)
    b. Dilute 1 ml of the stock standard with 4 ml of the porphyrin free urine (see step 6).
    c. Adjust pH to 5.2+0.1 with 2 N NaOH.
    d. Pour working standard through column.
    e. Add 5 ml of distilled water to the column. Let drain completely.
    f. Elute column with four 5 ml portions of 0.75 N HCl and take eluate to 25 ml volume with 0.75 N HCl.
    g. Mix eluate thoroughly with parafilm paper.
12. Read both the coproporphyrin and uroporphyrin eluate and the internal standard eluate in a fluorometer using 0.75 N HCl as a blank.

Calculations:
Whale Columns

-continued

Coproporphyrin: $\dfrac{U \times 0.1 \times 24 \text{ hr.}}{\text{Std.}}$ urine vol. = mcg per 24 hrs.

Uroporphyrin: (Using coproporphyrin Std.)

$\dfrac{U \times 0.074 \times 24 \text{ hr.}}{\text{Std.}}$ urine vol. = mcg per 24 hrs.

EXAMPLE II

1. A 24 hour urine sample is obtained, i.e., a sample including all urine excreted by a test subject over a 24 hour period, collected into a single container and preserved with sodium carbonate.

2. A 5.0 ml sample of well mixed 24 hour urine is placed in a 50 ml beaker.

3. Then, 1.0 ml of 1 M Tris Buffer (Tris (hydroxymethyl) amino-methane-HCl) is added to the beaker and the sample then adjusted to a pH of 5.2±0.1 by the addition of 1.5 N HCl.

4. An anionic ion exchange column is prepared for the sample (for each sample if multiple tests are being run).

5. After the ion exchange column is prepared, the buffered urine specimen is poured into a column. The resin in the column adsorbs substantially all of the porphyrins in the urine. The porphyrin-free buffered urine from the column is labeled and saved to be utilized for preparing the COPRO standard as described hereinafter.

6. Then the column is washed with 5 ml distilled water and drained to waste.

COPRO Elution and Measurement

7. The test column is placed above a 25 ml graduated cylinder.

8. Four, 5 ml portions of 0.3 N HCl are poured through the column and collected in the 25 ml graduated cylinder. This procedure results in the elution of substantially all COPRO. The column is then set aside for further testing for URO.

9. The COPRO containing eluate is then brought to a volume of 25 ml with additional 0.3 N HCl added with stirring directly to the graduated cylinder. If the eluate is not to be quantatively measured immediately, it is to be protected from evaporation and contamination and stored in the dark.

10. In quantitatively measuring the eluate sample for COPRO, it is necessary to have an internal standard. Such a standard is provided by dissolving a commercially known 5 mcg sample of COPRO in 10.0 ml of 1.5 N HCl and placed in a boiling water bath for about 5 minutes. Sigma Chemical Company provides such standardized 5 mcg samples of COPRO. The COPRO standard thus provided contains 0.5 mcg/ml COPRO. This standard, if kept in the dark, is stable and can be utilized over a period of up to at least one year. However, porphyrins are light-sensitive, decomposing rapidly in the light, and thus the COPRO standard, when not in actual use, should be stored in the dark.

11. For use as a standard, 1.0 ml of the 0.5 mcg/ml COPRO is mixed with 4 ml of porphyrin-free urine saved from step 5. The pH of the standard containing mixture is then adjusted to 5.2±0.1, for example, with 2 N NaOH.

12. The COPRO standard containing solution is then poured through a fresh ion exchange resin column of the type utilized and prepared in accordance with the process of step 4. Of course, the COPRO in the standard sample is substantially completely adsorbed by the ion exchange column.

13. Subsequently, 10.0 ml 0.3 N HCl is poured through the column to elute the known standard COPRO from the column.

14. The eluted COPRO standard from step 13, and the eluted COPRO of unknown concentration from step 9, are each measured with a fluorometer against a 0.3 N HCL blank and the concentration of the unknown COPRO calculated, as set forth hereinafter.

URO Elution and Measurement

15. The ion exchange column saved from step 8 is placed over a clean 25 ml graduated cylinder.

16. Then URO is eluted from the column with 6.2 ml of 3.0 N HCl, followed by further elution of 10 ml of distilled water. After these elutions the column need no longer be preserved.

17. The eluate in the graduated cylinder is then taken to a volume of 25 ml by the addition of water directly to the graduated cylinder. This brings the normality of the URO containing eluate to about 0.75 N. This eluate is then ready for measurement of URO concentration. If the eluate is not to be measured immediately, it should be covered to avoid evaporation and contamination and stored in the dark.

18. The URO eluate from step 17 is measured with a fluorometer in the same manner that the COPRO standard, and COPRO unknown were measured in step 14.

Calculations of COPRO and URO levels per 24 hours, utilizing the data obtained in the foregoing steps, is made as follows:

In the following equations:

B = the fluorometric reading of the 0.3 N HCl
$U_c$ = the fluorometric reading of the unknown COPRO sample
$U_u$ = the fluorometric reading of the unknown URO sample, and
$S_c$ = the fluorometric reading of the COPRO standard
mcg COPRO/24 hours = $(U_c - B \times 0.24 \times 24$ hour urine vol./$S_c - B)$ and;

mcg URO/24 hours = $(U_u - B \times 0.27 \times 24$ hour urine vol./$S_c - B)$

Using these techniques and calculations normal levels of COPRO are in the range of about 60 mcg to about 280 mcg/24 hours and normal levels of URO are in the range of about 10 mcg to about 50 mcg/24 hours.

The above equations are simplifications and were arrived at considering both the test procedures and collateral testing data.

The raw equation for determining mcg COPRO/24 hours is:

$$\dfrac{U_c - B}{S_c - B} \times \text{mcg of COPRO in the standard} \times \dfrac{\text{total ml of urine/24 hours}}{\text{of urine tested}}$$

then; as the standard was 25 ml containing 0.05 mcg COPRO/ml and as the aliquot volume of 24 hour urine tested was 5 ml, by substitution the equation becomes $$\text{mcg COPRO/24 hour} = \dfrac{U_c - B}{S_c - B} \times 1.25 \text{ mcg COPRO} \times \dfrac{\text{total ml urine/24 hours}}{5 \text{ ml}}$$

-continued $$= \frac{U_c - B}{S_c - B} \times 0.25 \times \text{total urine 24 hours}$$

However, upon applying standard addition and extraction studies for known quantities of COPRO and for combinations of COPRO and URO each added to porphyrin free urine to determine the efficiency of the separation of COPRO from URO using 0.3 N HCl as the eluent, it was found that about 4% of the URO was eluted with the COPRO, thus giving a COPRO reading of about 4% too high and a URO determination of about 4% too low. Applying this error to the formulas it was found that the calculation for COPRO should read as follows:

$$\text{mcg COPRO/24 hours} = \frac{V_c - B}{S_c - B} \times 0.25 \times 24 \text{ hr. vol.} \times (100\% - 4\%)$$

$$= \frac{U_c - B}{S_c - B} \times 0.24 \times 24 \text{ hour volume}$$

In a similar manner, the adjusted weight calculation for URO was calculated taking into account the 4% loss of URO during COPRO elution and data which was developed showing a quenching effect whereby a given concentration of URO in 0.75 N HCl fluoresces about 4% less than COPRO in 0.3 N HCl so that:

$$\text{mcg URO/24 hours} = \frac{U_u - B}{S_c - B} \times 0.25 \times 24 \text{ hr. vol.} \times$$

$$(100\% + 4\% + 4\%)$$

$$= \frac{U_u - B}{S_c - B} \times 0.27 \times 24 \text{ hour volume}$$

Experimental Procedure

The present quantitative system using ion exchange has identified eluents, and specifically hydrochloric acid eluents of various normalities which provide selective separation of COPRO from URO in human urine.

First, separate standard curves for COPRO and URO (mcg/ml prophyrin vs. fluorometric units) were constructed and used to estimate adsorption and elution of known porphyrin quantities from ion exchange resins.

Then 4 ml aliquots of porphyrin-free urine (raw urine previously passed through ion exchange resin) to which 1 ml of commercially supplied 0.5 mcg COPRO or URO are added separately and in combination with the aliquots. As in the preferred present process each sample was treated with 1 ml Tris buffer and the pH adjusted to 5.2±0.1. The various samples were then decanted into ion exchange columns, washed, and eluted consecutively with HCl of two different normalities. The first HCl eluent was of lesser normality, for elution of COPRO and the second HCl eluent was of higher normality for elution of URO.

Preliminary findings indicated that HCl in the range of about 0.1 N to about 0.4 N effectively eluted COPRO with minimum concomitant URO elution. Then a second consecutive elution using 2.5 ml 3.0 N HCl followed by 7.5 ml H$_2$O was used to remove the URO. Duplicate tests were set up wherein the first eluent consisted of 0.1 N, 0.2 N, 0.3 N, and 0.4 N HCl followed by a second eluent of 3.0 N HCl. Fluorometric measurements were taken of each eluate and the amount of COPRO and URO and the percent of COPRO and URO recovered determined by comparison with the previously prepared standard curves.

In Example II, upon determination of the most effective HCl normality for selective separation of COPRO from URO (i.e., 0.3 N), a second set of experiments was performed to estimate the percentage gain or loss of COPRO and URO from consecutive elutions. This was accomplished by spiking 4 ml porphyrin-free urine aliquots with 1 ml 0.5 mcg COPRO or URO, both separately and in combination. As in the preferred present process each sample was treated with 1 ml Tris buffer and the pH adjusted to 5.2±0.1. Samples were then passed though an ion exchange column and eluted with 10.0 ml 0.3 N HCl, the eluate collected and fluorometric units recorded. For elution of URO, the resin was treated with 2.5 ml 3.0 N HCl, followed by 7.5 ml H$_2$O. The total 10 ml volume of URO eluate was collected and fluorometric units recorded.

It was observed that nearly complete removal of either or both the COPRO and URO porphyrins from the ion exchange resin columns occured with these 10 ml elution processes.

The results of this testing regime are set forth in Table I.

TABLE I

| SELECTIVE SEPARATION OF COPRO AND URO PORPHYRINS | | | | |
|---|---|---|---|---|
| Urine Spiked | First Elution | | Second Elution | |
| With | HCl Normality | % Recovery | HCl Normality | % Recovery |
| 0.5 mcg COPRO | 0.1 | 64.6 | 3.0 | 30.0 |
|  | 0.2 | 85.3 | 3.0 | 12.5 |
|  | 0.3 | 90.0 | 3.0 | 10.0 |
|  | 0.4 | 100.7 | 3.0 | 2.0 |
| 0.5 mcg URO | 0.1 | 2.6 | 3.0 | 94.4 |
|  | 0.2 | 10.4 | 3.0 | 86.1 |
|  | 0.3 | 13.0 | 3.0 | 83.3 |
|  | 0.4 | 20.8 | 3.0 | 72.2 |
| 0.5 mcg COPRO | 0.1 | 66.1 | 3.0 | 105.5 |
| and 0.5 mcg URO | 0.2 | 88.1 | 3.0 | 94.4 |
|  | 0.3 | 94.5 | 3.0 | 88.8 |

It was found that 0.3 N HCl eluted 90% of the COPRO, when only COPRO was added to urine, but that 0.3 N HCl apparently eluted 94.5% of the COPRO when both COPRO and URO were added to urine. This indicates that 0.3 N HCl when used to make a COPRO separation in the presence of URO will elute about 4.5% of the URO.

The apparent approximate 4.5% increase in COPRO fluorescence and with 0.3 N HCl elution in the presence of URO was substantiated by recovery studies. See Table II.

TABLE II
RECOVERY STUDIES

|  |  | COPRO | URO | Apparent COPRO | Apparent URO |
|---|---|---|---|---|---|
| Eluent (HCl N) | = | 0.3 | 3.0 | 0.3 | 3.0 |
| Recovery (F.U.)X | = | 14.7 | 3.0 | 15.3 | 14.7 |
| Recovery Difference | = | — | — | +4.0% | −3.7% |
| | N = 14 | | | | |

Table II indicates that when COPRO and URO are present in combination there results an apparent 4.0% increase in COPRO fluorescense and an apparent 3.7% decrease in URO fluorescence. Taking this data into consideration, a 4% modification was used in deriving the COPRO and URO level equations as shown above.

Using the preferred process overall recovery of COPRO and URO using 0.3 N and 3.0 N HCl was 92%.

Experimental Data

To confirm the ability of 0.3 N HCl to selectively remove COPRO and URO containing samples adsorbed into an ion exchange resin with the elution of the remaining URO from the ion exchange resin with 3 N HCl, a commercially available abnormal urine supplied as Hyland Urine Control, Supplement, was obtained.

To this abnormal Hyland urine in aliquots of 5.0 ml was added Tris buffer and the pH adjusted to 5.2±0.1. The samples thus prepared were poured through an ion exchange column, washed with 5.0 ml H2O, and eluted in accordance with the preferred process of the present invention. The eluents obtained were measured fluorometrically and COPRO and URO levels determined using the above COPRO and URO equations and a fluorometrically measured URO standard.

The results are set forth in Table III.

TABLE III
COPRO AND URO RECOVERIES COMPARED WITH ESTIMATED ABNORMAL URINE

| Estimated Values for Abnormal Urine: | |
|---|---|
| COPRO | −312 mcg/l ± 94 |
| URO | −827 mcg/l ± 289 |

| Value measured by the method of the present invention: | | |
|---|---|---|
| | COPRO | URO |
| X = | 403 mcg/l ± 43 | 763 mcg/l ± 51 |
| S.D. = | 34.2 | 25.0 |
| C.V. = | 8.5% | 3.3% |
| N = | 13 | 13 |

It is thus seen that the process of the present invention is in close agreement with the estimated values for the abnormal urine.

Porphyrin Recovery from Raw Abnormal Urine

In a further test of the process of the present invention, there was obtained a 24 hour urine specimen from a patient diagnosed as having porphyria cutanea tarda. The laboratory diagnosis was based in part on a porphyrin screen.

Duplicate aliquots of urine were tested on three separate days using the same procedure as for Hyland abnormal urines, above.

Samples were also tested at an independent laboratory to confirm the above findings. The results are set forth in Table IV.

TABLE IV
PORPHYRIN RECOVERIES FROM RAW ABNORMAL URINE

| | COPRO | URO |
|---|---|---|
| X = | 1086 mcg/24 hr. ± 22 | 2327 mcg/24 Hr. ± 17 |
| S.D. = | 33.8 | 30.0 |
| C.V. = | 3.1% | 1.3% |
| N = | 6 | 6 |

It is seen that the process of the present invention confirms and agrees with the abnormal urine diagnosis; and that a very high precision is observed from data derived with estimated and unknown abnormal urines.

In summary, it is believed that the presently disclosed invention for the selective separation and quantitation of COPRO and URO prophyrin in urine by ion exchange is a reliable methodology showing high precision, dependability and accuracy. Its simplicity is not only advantageous over the qualitative porphyrin screen alone but also over other existing quantitative procedures.

We claim:

1. In the method for selective separation and quantitation of coproporphyrin and uroporphyrin in urine by ion exchange wherein a buffered urine sample is passed through an ion exchange resin and followed by washing non-adsorbed materials from the column, the steps comprising:
   eluting and collecting the adsorbed coproporphyrin present on the ionic exchange resin with a first normality of HCl;
   eluting and collecting the adsorbed uroporphyrin present on the ion exchange resin with a second normality of HCl differing from the first normality of HCl; and
   individually measuring the concentrations of the adsorbed coproporphyrin and uroporphyrin so collected against a known standard.

2. In the method according to claim 1, in which the coproporphyrin is eluted by a 0.75 N HCl.

3. In the method according to either of claims 1 or 2 in which the uroporphyrin is eluted by a 6.0 N HCl after the coproporphyrin has been eluted.

4. In the method according to either of claims 1 or 2 in which the concentrations of coproporphyin and uroporphyrin eluates are measured by fluorometric analysis.

5. In the method according to claim 4 further characterized by measuring the coproporphyrin and uroporphyrin eluates and comparing with a known standard eluate in a fluorometer using 0.75 N HCl as a blank.

6. The method of selective separation and quantitation of coproporphyrins and uroporphyrins in urine comprising the steps of:
   preparing a sample containing a mixture of porphyrins which may include coproporphyrins and uroporphyrins;
   adjusting the pH value of the mixture to a level on the order of 5.2±0.1;
   pouring a buffered sample into an ion exchange resin column containing an anionic ion exchange resin;
   washing the sample in the column with distilled water to remove non-adsorbed materials;
   eluting the coproprophyrin present in the column with a first normality of HCl;

eluting the uroporphyrin in the column with a second normality of HCl different from the first above normality;

agitating each eluate until a homogeneous sample is formed; and measuring the concentrations of coproporphyrin and uroporphyrin in each eluate against a known standard.

7. The method according to claim 6 wherein the eluate for coproporphyrins is on the order of 0.75 N HCl and the eluate for uroporphyrins is on the order of 6.0 N HCl.

8. The method according to claim 6 wherein the eluate for coproporphyrins is on the order of 0.3 N HCl and the eluate for uroporphyrins is on the order of 3.0 N HCl.

9. The method according to claim 6 wherein the ion exchange resin in the column is composed of AMBERLITE IRA-400 treated to provide ion exchange groups therein.

10. The method according to claim 6 in which said ion exchange resin is an anionic exchange resin and said porphyrin compounds are present in the sample in the form of anions.

11. The method according to claim 6 in which the concentrations of coproporphyrins and uroporphyrins are measured by fluorometric analysis.

* * * * *

UNITED STATES PATENT AND TRADEMARK OFFICE
CERTIFICATE OF CORRECTION

PATENT NO. : 4,236,892

DATED : December 2, 1980

INVENTOR(S) : Olga Duron, Richard J. Griffin

It is certified that error appears in the above—identified patent and that said Letters Patent is hereby corrected as shown below:

In The Specification:
Column 3, line 12, cancel "either" and substitute -- neither --.

Column 5, line 7, add:
-- Note: If running a uroporphyrin standard, use the same formula as coproporphyrin in calculating uroporphyrins.

Expected Values:
Coproporphyrins: 60-280 mcg/24 hrs.
Uroporphyrins: 10-50 mcg/24 hours. --

Column 7, line 17, cancel "Vc" and substitute -- Uc --.
Column 8, line 25, cancel "though" and substitute -- through --.
Column 9, line 7, cancel "X" and substitute -- $\underline{X}$ --.

In The Claims:
Claim 4, Column 10, line 47, cancel "coproporphyin" and substitute -- coproporphyrin --.
Claim 6, Column 10, line 67, cancel "coproporphyrin" and substitute -- coproporphyrin --.

Signed and Sealed this

Twenty-ninth Day of September 1981

[SEAL]

Attest:

GERALD J. MOSSINGHOFF

Attesting Officer    Commissioner of Patents and Trademarks